US011029249B2

(12) United States Patent
Hammond et al.

(10) Patent No.: US 11,029,249 B2
(45) Date of Patent: Jun. 8, 2021

(54) SAMPLE DETECTION DEVICE

(71) Applicant: UNIVERSITY COURT OF THE UNIVERSITY OF ST ANDREWS, Fife (GB)

(72) Inventors: Robert J. H. Hammond, Fife (GB); Stephen H. Gillespie, Fife (GB)

(73) Assignee: University Court of the University of St Andrews, St Andrews (GB)

( * ) Notice: Subject to any disclaimer, the term of this patent is extended or adjusted under 35 U.S.C. 154(b) by 0 days.

(21) Appl. No.: 16/461,919

(22) PCT Filed: Nov. 20, 2017

(86) PCT No.: PCT/GB2017/053479
§ 371 (c)(1),
(2) Date: May 17, 2019

(87) PCT Pub. No.: WO2018/091922
PCT Pub. Date: May 24, 2018

(65) Prior Publication Data
US 2019/0277759 A1    Sep. 12, 2019

(30) Foreign Application Priority Data
Nov. 18, 2016 (GB) ..................... 1619509

(51) Int. Cl.
*G01N 21/51* (2006.01)
*B01L 3/00* (2006.01)
(Continued)

(52) U.S. Cl.
CPC .............. *G01N 21/51* (2013.01); *B01L 3/502* (2013.01); *B01L 3/5027* (2013.01); *C12Q 1/04* (2013.01);
(Continued)

(58) Field of Classification Search
CPC .. B01L 3/5027; B01L 3/502; B01L 2200/026; B01L 2200/027;
(Continued)

(56) References Cited

U.S. PATENT DOCUMENTS 3,837,746 A * 9/1974 Acker .............. G01N 35/00594
356/440
5,164,796 A * 11/1992 Di Guiseppi .......... C12M 41/36
356/445
(Continued)

FOREIGN PATENT DOCUMENTS

WO    WO 2016/051267    4/2016

OTHER PUBLICATIONS

International Search Report prepared by the European Patent Office dated Dec. 21, 2017, for International Application No. PCT/GB2017/053479.
(Continued)

*Primary Examiner* — Sang H Nguyen
(74) *Attorney, Agent, or Firm* — Sheridan Ross P.C.

(57) ABSTRACT

An apparatus (150) comprises a first detection chamber (130) for receiving microorganisms and configured to allow detection of the microorganisms via detection of scattered light from the first detection chamber (130); a medium (120) configured to permit passage of microorganisms from a sample (110) through the medium (120) into the first detection chamber (130); and at least one second detection chamber (140) configured to allow detection of the microorganisms via detection of scattered light from the at least one second detection chamber (140).

33 Claims, 4 Drawing Sheets

(51) Int. Cl.
  *C12Q 1/04* (2006.01)
  *G01N 15/06* (2006.01)
  *G01N 15/00* (2006.01)
  *G01N 21/47* (2006.01)
  *G01N 21/11* (2006.01)

(52) U.S. Cl.
  CPC ........ *G01N 15/06* (2013.01); *B01L 2200/026* (2013.01); *B01L 2200/027* (2013.01); *B01L 2300/0681* (2013.01); *B01L 2300/0854* (2013.01); *B01L 2300/0864* (2013.01); *B01L 2300/0874* (2013.01); *B01L 2300/168* (2013.01); *G01N 21/11* (2013.01); *G01N 2015/0065* (2013.01); *G01N 2015/0693* (2013.01); *G01N 2021/4726* (2013.01); *G01N 2021/513* (2013.01)

(58) Field of Classification Search
  CPC ....... B01L 2300/168; B01L 2300/0681; B01L 2300/0854; B01L 2300/0864; B01L 2300/0874; G01N 21/51; G01N 15/06; G01N 21/11; G01N 2015/0693; G01N 2015/0065; G01N 2021/4726; C12Q 1/04
  See application file for complete search history.

(56) References Cited

U.S. PATENT DOCUMENTS

| | | | | |
|---|---|---|---|---|
| 5,525,475 | A * | 6/1996 | Ladouceur | G01N 33/5302 210/634 |
| 6,618,144 | B1 * | 9/2003 | Reed | G01N 15/0211 356/336 |
| 2002/0033939 | A1 * | 3/2002 | Hansen | G01N 15/1456 356/73 |
| 2003/0111607 | A1 * | 6/2003 | Bachur, Jr. | G01N 21/3504 250/343 |
| 2003/0153021 | A1 * | 8/2003 | Lu | C12Q 1/04 435/7.32 |
| 2007/0086916 | A1 * | 4/2007 | LeBoeuf | B82Y 30/00 422/400 |
| 2010/0273208 | A1 * | 10/2010 | Takenaka | C12M 41/36 435/34 |
| 2012/0003661 | A1 * | 1/2012 | Eckert | C12Q 1/04 435/6.15 |
| 2014/0377795 | A1 * | 12/2014 | Gannot | G01N 21/65 435/34 |
| 2015/0107993 | A1 * | 4/2015 | Izquierdo | G01N 33/1866 204/403.01 |
| 2016/0161404 | A1 * | 6/2016 | Marshall | B01L 3/50255 435/34 |
| 2016/0349178 | A1 * | 12/2016 | Walsh | G01N 21/272 |

OTHER PUBLICATIONS

Written Opinion prepared by the European Patent Office dated Dec. 21, 2017, for International Application No. PCT/GB2017/053479.
International Preliminary Report on Patentability for International (PCT) Patent Application No. PCT/GB2017/053479, dated May 31, 2019 17 pages.
Pickering et al. "Double-integrating-sphere system for measuring the optical properties of tissue," Applied Optics, Feb. 1993, vol. 32, No. 4, pp. 399-410.
Urban et al. "Characterization of Turbid Colloidal Suspensions using Light Scattering Techniques Combined with Cross-Correlation Methods," Journal of Colloid and Interface Science, 1998, vol. 207, pp. 150-158.
Varma et al. "Toward an ideal integrating nephelometer," Optics Letters, Jun. 15, 2003, vol. 28, No. 12, pp. 1007-1009.
Zhao et al. "A simple and accurate method for quantification of magnetosomes in magnetotactic bacteria by common spectrophotometer," Journal of Biochemical and Biophysical Methods, 2007, vol. 70, pp. 377-383.

* cited by examiner

Open state

Closed state

SAMPLE DETECTION DEVICE

CROSS REFERENCE TO RELATED APPLICATIONS

This application is a national stage application under 35 U.S.C. 371 and claims the benefit of PCT Application No. PCT/GB2017/053479 having an international filing date of 20 Nov. 2017, which designated the United States, which PCT application claimed the benefit of Great Britain Patent Application No. 1619509.1, filed 18 Nov. 2016, the disclosure of each of which are incorporated herein by reference.

The present invention relates to apparatuses and methods for measuring at least one characteristic of a sample, and in particular, though not exclusively, for measuring the presence and/or the growth of microorganisms in a biological sample, using light.

BACKGROUND OF THE INVENTION

Classic spectrophotometers can be used to determine optical properties of bacteria using absorption or scattering. Absorption spectrophotometers can be used to measure the relative absorbance of a sample. Absorbance is measured by comparing the intensity of light entering a sample with the intensity of light exiting the sample. A drop in light intensity indicates a quantity of light has been absorbed. This can be displayed as an arbitrary figure, typically an optical density. This can lead to an accurate count of the number of cells present in a sample.

Scattering spectrophotometers usually comprise an intense light source, such as a laser or a very bright incandescent source, and a monochromator. Light is incident on a sample and is scattered at different angles. Detectors placed at discrete intervals around a chamber collect the scattered light. Collected light in the side scattering region can be used to obtain information about granularity and light collected in the forward scattering region can be used to obtain information about the size of the particles. Overall intensity of the scattered light gives a turbidity reading and an indication of the number of particles present. In scattering spectrophotometers for measuring bacteria, the typical wavelength of the light source is 600 nm. This wavelength is the most scattered and least absorbed by a number of organic materials, such as DNA, proteins, cytochromes.

Flow cytometers can also determine properties of a sample of interest. When a sheath-flow of index matched liquid flows through a narrow tube, the liquid acts to reduce the lumen of the tube forcing cells in the liquid to pass through the tube individually. This facilitates cell counting. Laser light incident on the narrow tube is scattered as individual cells pass through. Side and forward scattering data can be recorded to give information about the size and granularity of the cells under study. Thousands of cells can pass through the beam and be measured in this way in a few seconds and in very little liquid. Whilst cytometers are useful in some applications, they are sophisticated machines that require extensive training of an operator. Safe operation also requires a regular input of reagents and this contributes to on-going running costs. The interpretation of data produced can also prove challenging.

Another method for measuring concentration of suspended particles in a liquid or gas is nephelometry. Nephelometers can be configured to use integrating spheres. In such a configuration, light is incident on a sample and may be scattered by particles in the sample before entering the integrating sphere. The scattered light is then reflected and diffused inside the integrating sphere before being detected at an exit port of the sphere. Unscattered light passes straight through the sphere and is not collected.

International Patent Application publication No. WO 2016/128747 (Hammond et al.), which is incorporated herein by reference, discloses a system for measuring a sample comprising: an integrating sphere light collector for collecting light and containing the sample; a light source for introducing light in the integrating sphere light collector, wherein the light source is operable to output light with a known modulation; a detector for detecting scattered light in the integrating sphere light collector and generating a signal indicative of the scattered light, and a lock-in amplifier operable use the known light modulation and the signal generated by the detector to provide an output for analysis.

While the system of WO 2016/128747 provides high sensitivity measurements of a sample such as a culture sample, there is a need in the prior art for new systems that can analyse samples directly at the point of care. In particular, there is a need in the prior art for systems that can be used to measure at least one characteristic, e.g. the presence of infectious microorganisms, of a primary clinical sample such as blood, urine, cerebrospinal fluid (CSF), pus, joint aspirate, or the like.

There is also a need in the prior art to provide systems or methods to allow determining not only the presence of infectious microorganisms in a clinical sample, but also the susceptibility of such microorganisms to potential therapeutic substances such as antibiotics.

SUMMARY OF THE INVENTION

According to a first aspect of the present invention, there is provided an apparatus comprising:

a first detection chamber for receiving microorganisms and configured to allow detection of the microorganisms via detection of scattered light from the first detection chamber;

a medium configured to permit passage of microorganisms from a sample through the medium into the first detection chamber; and at least one second detection chamber configured to allow detection of the microorganisms via detection of scattered light from the at least one second detection chamber. The scattered light may comprise light that has been transmitted into the respective sample chamber and scattered by the microorganisms in said sample chamber.

The medium may comprise a membrane. The medium may be semipermeable. The medium may comprise a semipermeable membrane. The medium may be configured to allow passage of the microorganisms and to block passage of at least some other particles or fluid that may be present.

The detection of the microorganisms may comprise detection of the presence or absence of the microorganisms and/or measurement of at least one property of the microorganisms, for example a measurement of, or representative, a number or amount of the microorganisms.

Advantageously, the first detection chamber is configured to allow quantitative measurement of the microorganisms via detection of scattered light from the first detection chamber. Advantageously also, the at least one second detection chamber is configured to allow quantitative measurement of the microorganisms via detection of scattered light from at least one second detection chamber.

Advantageously, the sample may be a primary or clinical sample, such as blood, urine, cerebrospinal fluid (CSF), pus, joint aspirate, another bodily fluid, or the like. Thus, the apparatus may be used to measure and/or analyse samples directly at the point of care, and may therefore be termed a "point-of-care" device.

The microorganisms may comprise pathogenic microorganisms, e.g. bacteria.

The apparatus may comprise a specimen chamber for receiving the sample, e.g. the clinical sample. The specimen chamber and the first detection chamber may form separate chambers. The apparatus may have walls defining the specimen chamber and the first detection, respectively. An opening may be provided between the specimen chamber and the first detection, e.g. within the walls thereof. The semipermeable medium may be provided within the opening and/or may cover substantially the whole area of the opening. The semipermeable medium may be configured to permit passage of the microorganisms from the specimen chamber into the detection chamber. The first detection chamber may contain, e.g., may be filled or partially filled with, a fluid such as a bacterial growth fluid. By such provision, any microorganisms passing through the membrane into the first detection chamber may survive and/or may be able to grow inside the first detection chamber.

The membrane may be configured to selectively allow passage of microorganisms, e.g., bacteria, from the sample in the first detection chamber. The membrane may be configured to prevent passage of larger components, e.g. cellular components. The semipermeable membrane may have a pore size of greater than 2 µm with the upper limit of pore size only defined by what is possible with current technology. In one embodiment, the semipermeable membrane may have a pore size in the range of 2-10 µm (or greater), e.g., 2-5 µm.

The membrane may be made from any suitable material, such as a polymeric material, e.g. nitrocellulose, polyamide, or the like, a metallic material, e.g. aluminium, or the like. It will be appreciated that the particular type of membrane and associated pore size may be selected by a person of skill in the art depending on the particular application for which the apparatus is intended to be used. In particular, a desired pore size may be selected to allow passage of a specific type of bacteria. By way of example, for detection of non-tuberculosis mycobacteria (NTM) the pore size may be in the range of 4-5 µm. For a less filamentous and more common human pathogen such as *E. coli* the pore size might be 3-4 µm.

The apparatus may further comprise a first light source for emitting light into the first detection chamber. The first light source may comprise a laser or a LED. The first light source may be located external to the first detection chamber. The light source may have a wavelength in the range of 590 nm to 650 nm, for example 635 nm. Alternatively, the light source may have a wavelength in the range of 620 nm to 750 nm, for example 635 nm. It will be appreciated that any wavelength may be selected so long as it is capable of being scattered by microorganisms present in the first detection chamber.

The apparatus may comprise a signal generator for generating a control signal to cause the first light source to output modulated light.

The apparatus may further comprise a first detector for detecting scattered light from the first chamber and generating a signal indicative of the scattered light. The first detector may be located external to the first detection chamber.

The first detection chamber may be capable of reflecting light emitted by the light source inside the first detection chamber. The first detection chamber may comprise or may be defined by one or more walls. The wall(s) may be provided with and/or may comprise a reflective material, such as aluminium, silver, titanium oxide, or the like. In one embodiment, an outer surface of the first detection chamber, e.g. wall(s) thereof, may be covered or coated with the reflective material. By such provision the reflective material may not directly interfere with the microorganisms. In another embodiment, the matrix defining the first detection chamber, e.g. the walls thereof, may contain the reflective material, which may for example be provided in particulate form within the matrix forming the wall(s) of the first detection chamber. Advantageously, the membrane may also be made of or may contain or may be coated with a reflective material in order to reflect inwardly any light emitted inside the first detection chamber.

The first detection chamber may have a first light entry aperture, which may comprise or be referred to as a first entry point, to allow light emitted by the first light source to enter the first detection chamber. The first entry point may define an area of the first detection chamber devoid of any reflective material.

The first detection chamber may have a first light exit aperture, which may comprise or be referred to as a first exit point, located opposite the first entry point. The first exit point may define an area of the first detection chamber devoid of any reflective material. By such provision, in the absence of any microorganisms in the first detection chamber, light emitted by the first light source will travel in a straight line through the first detection chamber and exit through the first exit point.

The first detection chamber may also have a light detection outlet which may be associated with the first detector. The light detection outlet may be, or may define an area of the first detection chamber, devoid of any reflective material. The detection outlet may allow scattered light to exit the first detection chamber and be collected by the first detector in order to generate a signal indicative of the scattered light. The detection outlet may be located in a region of the first detection chamber separate and/or distal from the first inlet point and the first exit point. By such provision, only scattered light may exit the first detection chamber through the detection outlet.

The apparatus may comprise a lock-in amplifier operable to use a signal from the signal generator indicative of the light modulation and the signal generated by the first detector to provide an output for analysis.

The at least one second detection chamber may be configured to measure and/or determine the growth of the microorganisms via detection of scattered light through the chamber.

In one embodiment, the apparatus may comprise a plurality of second detection chambers. One or more chambers may contain or may be provided with a substance potentially capable of inhibiting the growth of the microorganisms. For example, one or more chambers may contain an antibiotic. Advantageously, different antibiotics may be provided in different chambers. By such provision, the apparatus may permit determination of the susceptibility of the microorganisms to different antibiotics. One or more, e.g. one, of the second detection chamber may be devoid of any antibiotic, and thus may be and/or may act as a control chamber. In use, after an amount of time sufficient to detect bacterial growth, the absence of bacteria growth in one of the other second detection chambers may be indicative of the susceptibility of the bacteria to the substance, e.g. antibiotic, present in that chamber. The substance, e.g. antibiotic, may be present in one or more chambers in freeze-dried form, which may provide prolonged shelf-life without compromising the activity or efficacy of the antibiotic. Alternatively, the substance, e.g. antibiotic, may be present in one or more chambers in fluid form, e.g. as an aqueous solution.

The second detection chamber(s) may be configured to be in fluid communication with the first detection chamber.

Advantageously, the apparatus may comprise a transfer mechanism to allow transfer, e.g. selective transfer, of at least part of a sample from the first detection chamber to the second detection chamber(s).

The transfer mechanism may comprise a micro- or macro-fluidic mechanism capable of transferring at least part of a sample from the first detection chamber to the second detection chamber(s). For example, the transfer mechanism may comprise one or more micro- or macro-fluidic channels between the first detection chamber and the second detection chamber(s), which may be able to transfer at least part of a sample via actuation of a pump, a vacuum system, or the like.

The transfer mechanism may comprise one or more valves, e.g. one-way valves, to allow transfer at least part of a sample between the first detection chamber and the second detection chamber(s). In one embodiment, each second detection chamber(s) is separated from the first detection chamber by a respective valve. In use, when no transfer of the sample, e.g. microorganisms, to the second detection chamber(s) is required, the valve(s) may be closed. When transfer of the sample to the second detection chamber(s) is required, e.g. after identification or measurement of an infectious microorganism in the first detection chamber, the valves may be opened so as to allow transfer thereof into a respective second detection chamber(s). In one embodiment, the one-way valve(s) may be gravity operated.

At least part of the apparatus may be provided as a cartridge which may be fitted or inserted into the apparatus, e.g. into a detection system thereof. Conveniently, the cartridge may comprise the specimen chamber, first detection chamber and second detection chamber(s). The cartridge may further comprise the semipermeable medium. This may allow a user to dispose of the cartridge containing the sample after analysis is complete. The cartridge may also comprise at least part of the transfer mechanism, e.g. the valve(s). The apparatus may comprise or may define a cartridge-receiving portion configured to receive the cartridge.

Conveniently, when the transfer mechanism comprises one or more gravity-operated one-way valves, the cartridge may be placed in a pre-determined orientation to open the valve(s) e.g. the cartridge may be placed upside-down in the apparatus so as to open the one or more one-way valves. This arrangement provides a simple, effective and reliable mechanism for transferring part of the sample from the first detection chamber to the second detection chamber(s).

The apparatus may comprise at least one second light source for emitting light into one or more second detection chambers. Alternatively, the first light source may be used to emit the light into the second detection chambers. Thus, the second light source(s) may be the same as the first light source or may be different. When the at least one second light source(s) is the same as the first light source (i.e. no distinct second light source is provided) there may be provided a mechanism, e.g. a beam splitter and/or an optical switch, for selectively directing the light emitted by the light source to one or more second detection chambers. When the at least one second light source(s) is separate or distinct from the first light source, there may also be provided a mechanism, e.g. a beam splitter and/or an optical switch, for selectively directing the light emitted by the second light source to the second detection chamber(s). Alternatively or additionally, there may be provided a separate dedicated second light source for each of the second detection chambers. The at least one second light source(s) may of the same or similar type to the first light source(s).

The apparatus may comprise a signal generator for generating a control signal to cause the at least second light source to output modulated light.

The apparatus may further comprise at least one second detector for detecting scattered light in one or more of the second detection chambers and generating a signal indicative of the scattered light. The at least one second detector may be located external to the second detection chamber(s). The at least one second detector may be the same as the first detector or may be different.

Each second detection chamber may be capable of reflecting light emitted by the light source into the second detection chamber. For example, each second detection chamber may be configured to reflect the light multiple times. Each second detection chamber may comprise or may be defined by one or more walls. The wall(s) may be provided with and/or may comprise a reflective material, such as aluminium, silver, titanium oxide, or the like. In one embodiment, an outer surface of the second detection chamber(s), e.g. wall(s) thereof, may be covered or coated with the reflective material. In another embodiment, the matrix defining the second detection chamber(s), e.g. the walls thereof, may contain the reflective material, which may for example be provided in particulate form within the matrix forming the wall(s) of each second detection chamber.

Each second detection chamber may have a respective light entry aperture, which may comprise or be referred to as a second entry point, to allow the second light source to emit light into the second detection chamber(s). Each second entry point may define an area of a respective second detection chamber devoid of any reflective material.

Each second detection chamber may have a respective light exit aperture, which may comprise or be referred to as a second exit point, and which may for example be located opposite the second entry point. The second exit point may define an area of a respective second detection chamber devoid of any reflective material.

Each second detection chamber may also have a detection outlet which may be associated with the second detector. The detection outlet may be, or may define an area, devoid of any reflective material. The detection outlet may allow scattered light to exit a respective second detection chamber and be collected by the second detector in order to generate a signal indicative of the scattered light. The detection outlet may be located in a region of a respective second detection chamber separate and/or distal from the second inlet point and the second exit point. By such provision, only scattered light may exit the second detection chamber through the detection outlet.

When the at least one second detector is the same as the first detector (i.e. no distinct second detector is provided), there may be provided a mechanism, e.g. a beam splitter and/or an optical switch, for selectively directing the scattered light exiting each second detection chamber via a respective second exit point to the detector. There may be provided a mechanism, e.g. a beam splitter and/or an optical switch, for selectively directing the scattered light exiting each second detection chamber via a respective second exit point to the second detector. Alternatively or additionally, there may be provided a plurality of second detectors with a separate dedicated one of the second detectors for each second detection chamber.

The first detection chamber and/or the second detection chamber(s) may made from a transparent material, e.g. glass or a polymeric material such as polycarbonate, polypropylene, polyethylene, or the like. By such provision, any region of the first detection chamber and/or the second detection chamber(s) not covered, coated, or provided with a reflective material is capable of transmitted light, e.g. light emitted by the first light source and/or the second light source. At least part of the cartridge, e.g. the specimen chamber, first detection chamber and/or second detection chamber(s) may be made from a transparent material. In an embodiment, the cartridge may be one-piece and/or may be formed integrally from the transparent material.

According to a second aspect of the invention there is provided a device for use in the apparatus according to the first aspect, the device comprising:

a first detection chamber for receiving microorganisms and configured to allow detection of the microorganisms via detection of scattered light from the first detection chamber;

a medium configured to permit passage of microorganisms from a sample through the medium into the first detection chamber; and at least one second detection chamber configured to allow detection of the microorganisms via detection of scattered light from the second detection chamber. The medium may comprise a membrane. The medium may be semipermeable. The medium may comprise a semipermeable membrane The medium may be configured to allow passage of the microorganisms and to block passage of at least some other particles or fluid that may be present.

The device may comprise a specimen chamber for receiving a sample, e.g. a clinical sample. The specimen chamber and the first detection chamber may form separate chambers. The semipermeable medium may be configured to permit passage of the microorganisms from the specimen chamber into the detection chamber.

The device may comprise a plurality of second detection chambers. One or more chambers may contain or may be provided with a substance potentially capable of inhibiting the growth of the microorganisms.

The second detection chamber(s) may be configured to be in fluid communication with the first detection chamber.

Advantageously, the device may comprise a transfer mechanism to allow transfer, e.g. selective transfer, of at least part of a sample, e.g. some of the microorganisms, from the first detection chamber to the second detection chamber(s).

The device may define or may be configured as a cartridge which may be fitted or inserted into the apparatus according to the first aspect. Conveniently, the cartridge may comprise the specimen chamber, first detection chamber and second detection chamber(s). The cartridge may further comprise the semipermeable medium. This may allow a user to dispose of the cartridge containing the sample after analysis is complete. The cartridge may also comprise at least part of the transfer mechanism, e.g. the valve(s) and/or micro- or macro-fluidic channel(s).

Conveniently, when the transfer mechanism comprises one or more gravity-operated one-way valves, the cartridge may be placed in a pre-determined orientation to open the valve(s) e.g. the cartridge may be placed upside-down in the apparatus so as to open the one or more one-way valves. This arrangement provides a simple, effective and reliable mechanism for transferring part of the sample from the first detection chamber to the second detection chamber(s).

The features described in respect of any other aspect of the invention are equally applicable to the device according to the second aspect, and are therefore not repeated here for brevity.

According to a third aspect of the invention there is provided a method for monitoring a biological material, the method comprising:

introducing a biological sample into a specimen chamber of an apparatus;

allowing selective passage of microorganisms from the specimen chamber through a medium into a first detection chamber;

emitting light into the first detection chamber so that the light at least partly passes through and is scattered by the sample, and detecting light scattered in the first detection chamber. The method may comprise analysing the detected light, wherein the detected light may be indicative of an amount of microorganisms in the biological material.

The method may comprise transferring of at least part of the sample from the first detection chamber to at least one second detection chamber, for example in response to microorganisms being detected in the first detection chamber. The at least one second detection chamber may comprise a plurality of second detection chambers.

The method may comprise monitoring the detected light over time, or detecting the light in response to expiry of a predetermined period of time after introduction of the biological sample.

The method may further comprise emitting light into at least one second detection chamber so that the light passes through and is scattered by the sample, detecting light scattered in the at least one second detection chamber and analysing the detected light, wherein changes in the captured light as a function of time are indicative of a change in the biological material.

Advantageously, the biological sample may comprise or may be a clinical sample, preferably a primary clinical sample such as blood, urine, cerebrospinal fluid (CSF), pus, joint aspirate, or the like. Thus, the method may be used directly at the point of care of a subject or patient. The sample may comprise microorganisms, e.g. pathogenic microorganisms such as bacteria and/or microbes.

The method may comprise analysing the scattered light detected from the first detection chamber so as to allow quantitative measurement of the microorganisms. The method may comprise determining the presence and/or the amount of microorganisms in the first detection chamber.

The method may comprise analysing the scattered light detected from one or more second detection chamber(s) so as to allow quantitative measurement of the microorganisms. The method may comprise determining the growth of microorganisms in one or more second detection chamber(s), e.g. in each second detection chamber, over time, e.g. over a predetermined amount of time. Thus the method may comprise determining susceptibility of microorganisms to one or more substances, e.g. antibiotics, provided within one or more respective second detection chambers.

The apparatus may comprise, or may be as defined in, the apparatus according to the first aspect of the invention.

Advantageously, the method may allow a user to determine not only the presence of infectious microorganisms in a clinical sample, but also the susceptibility of such microorganisms to potential therapeutic substances such as antibiotics.

The features described in respect of any other aspect of the invention are equally applicable to the method according to the third aspect, and are therefore not repeated here for brevity.

Features in one aspect may be applied as features in any other aspect, in any appropriate combination. For example, any one of device, apparatus or method features may be applied as any other of device, apparatus or method features.

BRIEF DESCRIPTION OF THE DRAWINGS

Various aspects of the invention will now be described by way of example only, and with reference to the accompanying drawings, in which.

DETAILED DESCRIPTION

Figure 1:
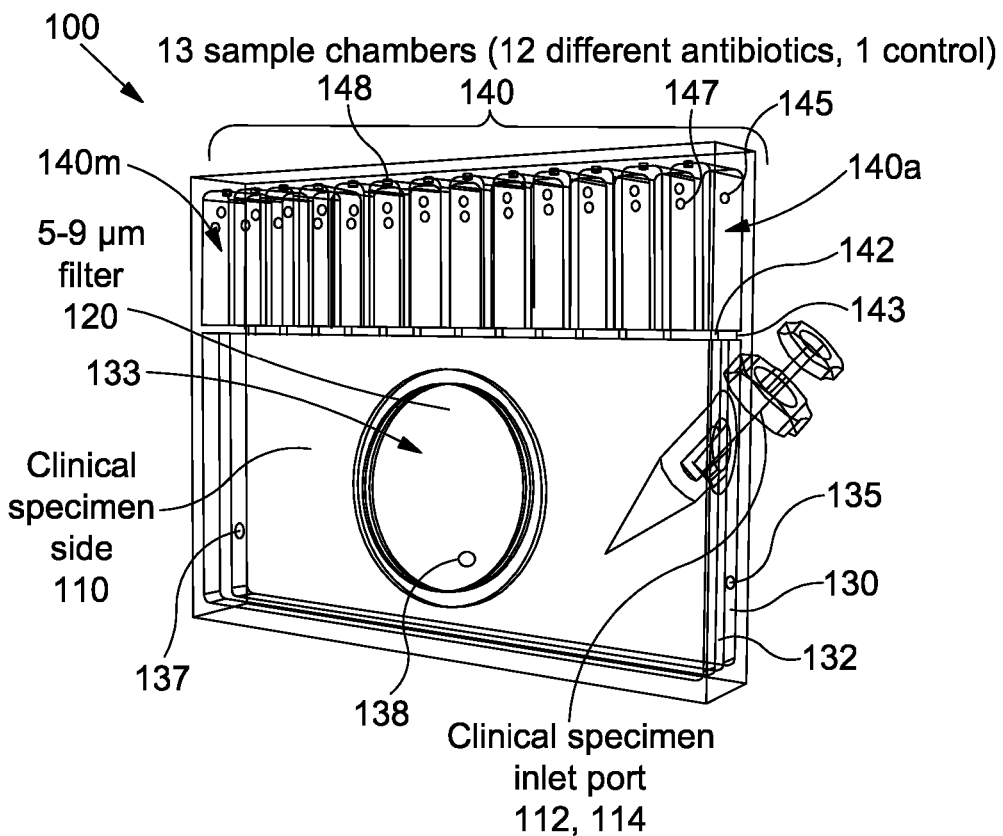
FIG. 1 is a perspective wireframe view of a cartridge for use in an apparatus, according to an embodiment of the present invention.

Referring to FIG. 1 there is shown a perspective wireframe view of a cartridge, generally designated 100, according to an embodiment of the present invention.

Figure 5:
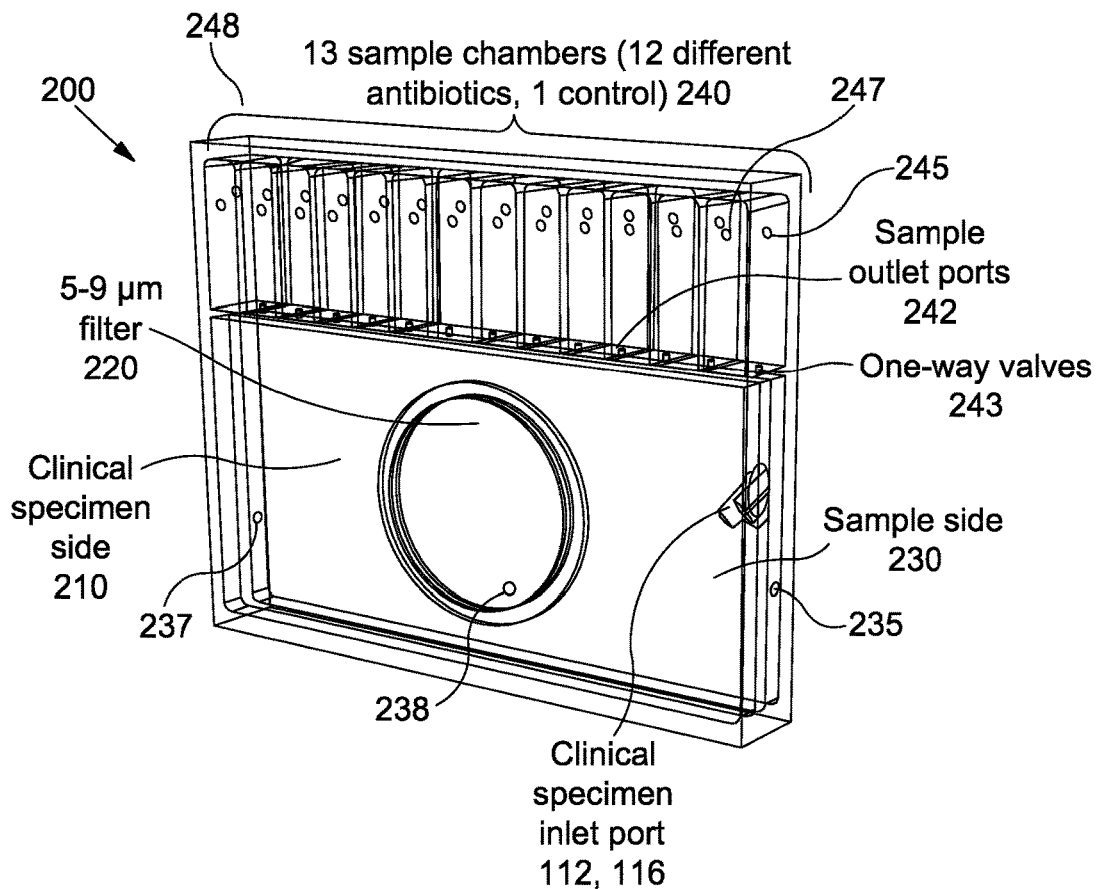
FIG. 5 is a perspective wireframe view of a cartridge for use in an apparatus, according to another embodiment of the present invention.

The cartridge 100 has a specimen chamber 110 configured to receive a sample, in this embodiment a clinical sample such as blood, urine, cerebrospinal fluid (CSF), pus, joint aspirate, another bodily fluid, or the like. The cartridge 100 has a sample feed arrangement 112 to allow a user to feed the clinical sample into the specimen chamber 110. In this embodiment, the sample feed arrangement 112 is a Luer lock type arrangement 114. However, any other type of feeding arrangement may be envisaged which permits effective delivery of the sample into the specimen chamber 110, for example the alternative arrangement as shown in FIG. 5.

The cartridge 100 has a semipermeable membrane 120 which allows passage of microorganisms from the specimen chamber 110 into a first detection chamber 130.

In this embodiment, the specimen chamber 110 and the first detection chamber 130 define substantially cuboid volumes separated by a first wall 132. The first wall 132 has an opening 133. The semipermeable membrane 120 occupies substantially the whole area of the opening 133 such that the membrane 120 provides an interface between the specimen chamber 110 and the first detection chamber 130.

The membrane 120 is configured to permit passage of bacteria from the specimen chamber 110 into the first detection chamber 130. The first detection chamber 130 is filled or partially filled with a fluid such as a bacterial growth fluid, such that any bacteria passing through the membrane 120 into the first detection chamber 130 is able to survive and/or grow inside the first detection chamber 130.

Figure 2:
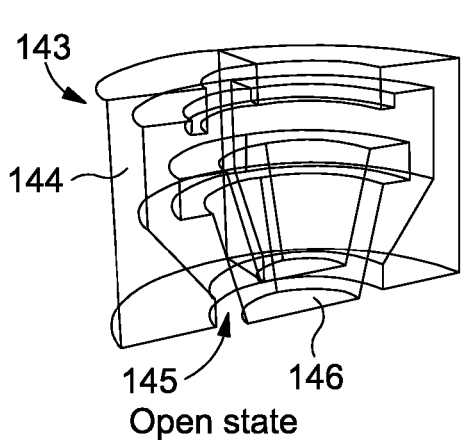
FIG. 2 is a perspective wireframe view of a valve for use in the cartridge of FIG. 1, in an open configuration.
Figure 3:
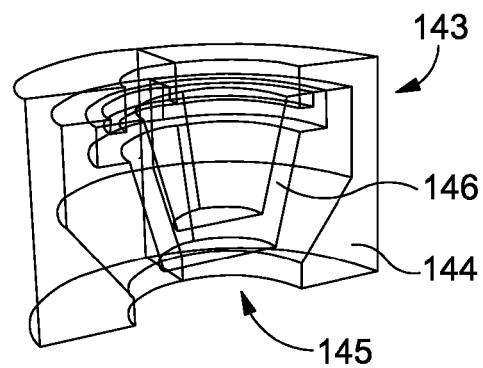
FIG. 3 is a perspective wireframe view of a valve for use in the cartridge of FIG. 1, in a closed configuration.

The cartridge 100 also has a plurality of second detection chambers 140, in this embodiment thirteen second detection chambers 140a-140m. The second detection chambers 140 are in fluid communication with the first detection chamber 130 via channels 142 each equipped with a gravity-operated one-way valve 143, which are best shown in FIGS. 2 and 3. It will be appreciated that alternative transfer mechanisms may be envisaged to allow transfer of the medium containing bacteria from the first detection chamber 130 into the second detection chambers 140, such as micro- or macro-fluidic channels which may be associated with an operable pump, vacuum system or the like.

The cartridge 100, and in particular the first detection chamber 130 and the second detection chambers 140, are made of a transparent material, for instance a transparent plastic material such as polycarbonate, polypropylene, polyethylene, or the like.

The first detection chamber 130 is provided with and/or comprises a reflective material, such as aluminium, silver, titanium oxide, or the like, in order to reflect inwardly any light emitted inside the first detection chamber 130. Preferably, the semipermeable membrane 120 is also made of or contains a reflective material in order to reflect inwardly any light emitted inside the first detection chamber 130.

Each second detection chamber 140 is provided with and/or comprises a reflective material, such as aluminium, silver, titanium oxide, or the like, in order to reflect inwardly any light emitted inside each of the second detection chambers 140.

Figure 4:
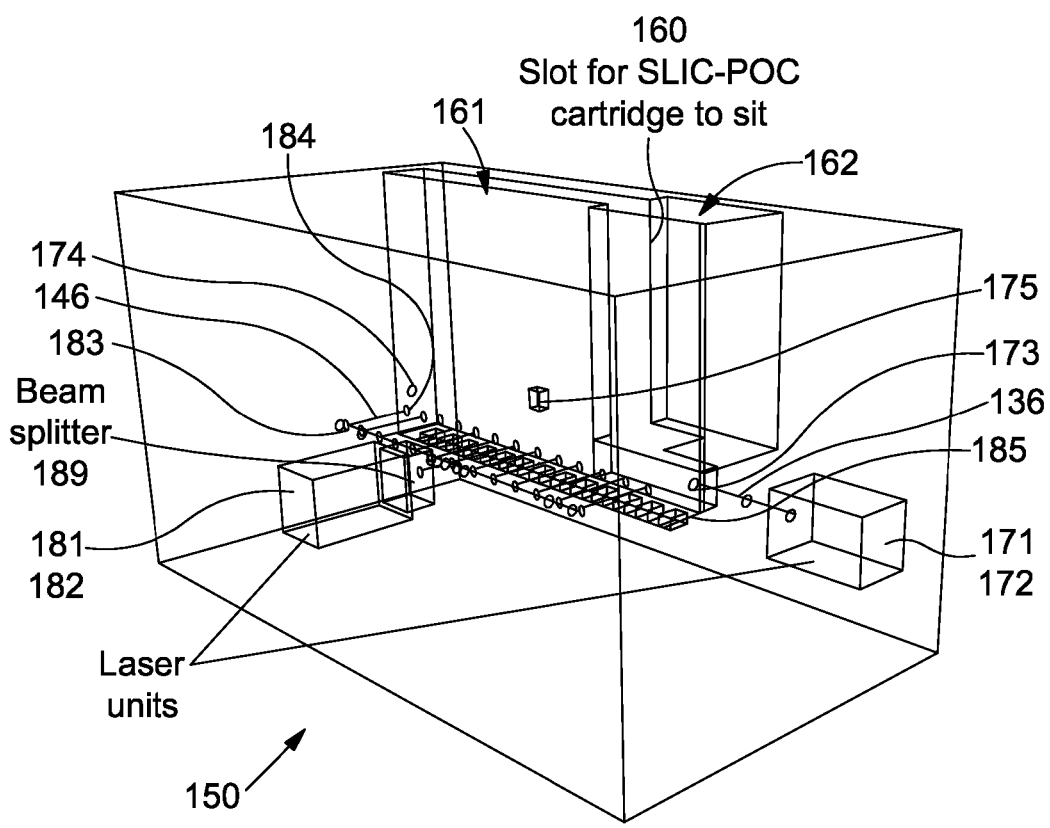
FIG. 4 is a perspective wireframe view of an apparatus according to an embodiment of the present invention, for use with the cartridge of FIG. 1.

In use, referring to FIG. 4, the cartridge 100 is placed within the receiving portion 160 of detection apparatus 150.

The receiving portion 160 has a generally elongate cuboid shape, and in this embodiment has a narrow portion 161 and a wide portion 162. The width of the narrow portion is dimensioned such that the receiving portion can accommodate the cartridge 100, and is therefore slightly greater than the width of the cartridge. As explained in relation to FIG. 1, the cartridge has a sample feed arrangement 112, which, in the embodiment of FIG. 1, is a Luer lock type arrangement 114, and which therefore creates a protrusion in the width of the cartridge in the region of the Luer lock. Thus, the wide portion 162 of the receiving portion 160 of the apparatus allows the receiving portion 160 to accommodate the cartridge.

As will be later described in more detail, the cartridge 100 can be removed from the receiving portion 160 and inserted in the receiving portion 160 upside down in order to carry out measurements in the second detection chambers 140. As shown in FIG. 4, the wide portion 162 extends width-wise on both sides of the narrow portion 161 in order to allow the receiving portion 160 to accommodate the cartridge 100 in both configurations, i.e., with the protrusion created by the Luer lock arrangement 114 facing either forward or rearward in the wide portion 162 of the receiving portion 160.

The detection apparatus 150 has a first light source 171 which in this embodiment is a first laser unit 172.

The first detection chamber 130 has a first entry point 135 aligned with aperture 173 and devoid of any reflective material so as to allow light emitted by the first light source 171 to enter the first detection chamber 130 via first conduction tube 136. In this embodiment, the first laser unit 172 is located such that the light emitted into the first detection chamber 130 interacts with the sample throughout the length of the first detection chamber 130. By such provision, the emitted light passes through more of the sample, thus increasing the potential for scattering and therefore increasing sensitivity.

The first detection chamber 130 has a first exit point 137 located opposite the first entry point 135 and aligned with aperture 174 and also devoid of any reflective material so as to allow unscattered light passing through the sample to exit the first detection chamber 130 where the light may be absorbed by a beam dump or a baffle.

The apparatus further comprises a first detector 175 located external to the first detection chamber 130 for detecting scattered light and generating a signal indicative of the scattered light. The first detection chamber 130 has a detection outlet 138 aligned with and associated with the first detector 175. The detection outlet 138 is devoid of any reflective material so as to allow scattered light to exit the first detection chamber 130 and be collected by the first detector 175 in order to generate a signal indicative of the scattered light.

In this embodiment, when the signal generated by the first detector 175 and associated components (described in more detail in relation to FIG. 7) indicates the presence of a pathogenic amount of microorganisms, e.g. bacteria, the sample may further undergo a susceptibility test. The cartridge 100 is removed from the receiving portion 160 and re-inserted therein upside down, such that the second detection chambers 140 face downwards.

As best illustrated in FIGS. 2 and 3, the second detection chambers 140 are in fluid communication with the first detection chamber 130 via channels 142 each equipped with a gravity-operated one-way valve 143. Each valve 143 has a body portion 144 defining and passage 145 and a complementary movable gate 146. The gate is movable vertically under the influence of gravity. In a closed configuration, when the first detection chamber 130 is below the second detection chambers 140, the movable gate 146 engages the body portion 144 under its own weight such that the passage 145 is closed. When the cartridge 100 is placed in the receiving portion 160 upside down and the first detection chamber 130 is above the second detection chambers 140, the movable gates 146 drop under their own weight, moving away from a respective body portion 144 and causing the valves 143 to open. The sample containing microorganisms can thus flow under gravity from the first detection chamber 130 into the second detection chambers 140. This arrangement permits transfer of the sample from the first detection chamber 130 into the second detection chambers 140 without the need for additional parts or equipment such as microfluidic pumps, vacuum systems, or the like. However, it will be appreciated that other transfer mechanisms may be envisaged to transfer a sample from the first detection chamber 130 into the second detection chambers 140, such as microfluidic pumps, vacuum systems or the like, which may allow transfer of the sample without the need for removal and reinsertion of the cartridge 100 into the apparatus 150.

Referring back to FIG. 4, the detection apparatus 150 has a second light source 181 which in this embodiment is a second laser unit 182. In this embodiment, the apparatus 150 has a beam splitter 189 capable of selectively directing the light emitted by the second laser unit 182 to each of the second detection chambers 140. However, it will be appreciated that in other embodiments a separate laser unit may be provided for each of the second detection chambers 140.

As shown in FIG. 1, each second detection chamber 140 has a first entry point 145 aligned with aperture 183 and devoid of any reflective material so as to allow light emitted by the second laser unit 182 to enter the second detection chambers 140 via respective second conduction tubes 146.

Each second detection chamber 140 has a second exit point 147 located opposite a respective second entry point 145 and aligned with aperture 184 and also devoid of any reflective material so as to allow unscattered light passing through the sample to exit the second detection chamber 140 where the light may be absorbed by a beam dump or a baffle.

The apparatus further comprises second detectors 185 located external to a respective second detection chamber 140 for detecting scattered light and generating a signal indicative of the scattered light. Each second detection chamber 140 has a detection outlet 148 aligned with and associated with a respective second detector 185. Detection outlets 138 are devoid of any reflective material so as to allow scattered light to exit the second detection chambers 140 and be collected by the second detectors 185 in order to generate a signal indicative of the scattered light.

In this embodiment, each second detection chamber 140 has an associated second detector 185. However, it will be appreciated that in other embodiments, there may be provided a single second detector and an associated mechanism, e.g. a beam splitter and/or an optical switch, for selectively directing the scattered light exiting each second detection chamber to the second detector.

In this embodiment, twelve (140b-140m) of the thirteen chambers 140 contain an antibiotic, and one chamber (140a) acts as a control chamber. In use, the signal from each second detector 185 is measured over time. A change in the signal in the control chamber 140a, and in particular an increase in measured scattered light in the control chamber 140a, is indicative of growth of the microorganisms over that period of time. This is compared with the measured scattered light in the other chambers 140b-140m, and the absence of an increased signal over the period of time in one or more chambers 140b-140m is indicative of the absence of growth of the microorganisms over that period of time, and thus of the susceptibility of the microorganism to the substance, e.g. antibiotic, present in that or those chambers.

Referring to FIG. 5 there is shown a perspective wireframe view of a cartridge, generally designated 200, according to another embodiment of the present invention.

The cartridge 200 of FIG. 5 is generally similar to the cartridge of FIG. 1, like parts denoted by like numerals, incremented by '100'. However, while the sample feed arrangement 112 of the cartridge 100 of FIG. 1 is a Luer lock type arrangement 114, the sample feed arrangement 212 of the cartridge 200 of FIG. 5 is an inlet port 216 in fluid communication with the first detection chamber 230. Thus, in this embodiment, the sample feed arrangement 212 does not create any outwards protrusions, and the cartridge has a generally rectangular cross-section. As a result, as shown in FIG. 6, the complementary shape of the receiving portion 260 of the detection apparatus 250 is also rectangular in cross-section, and is devoid of a wider portion 160 which was required in the apparatus of FIG. 4.

Figure 6:
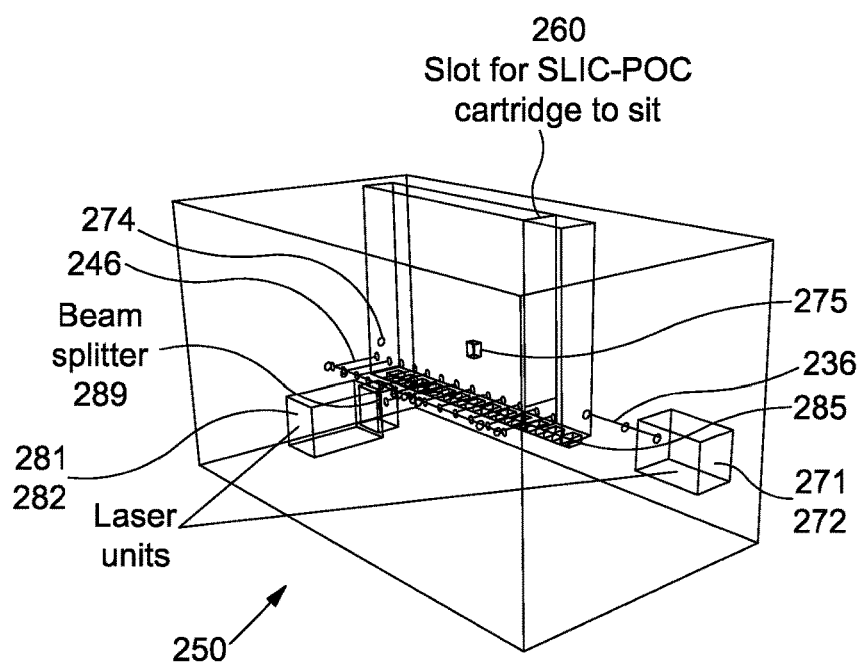
FIG. 6 is a perspective wireframe view of an apparatus for use with the cartridge of FIG. 5.
Figure 7:
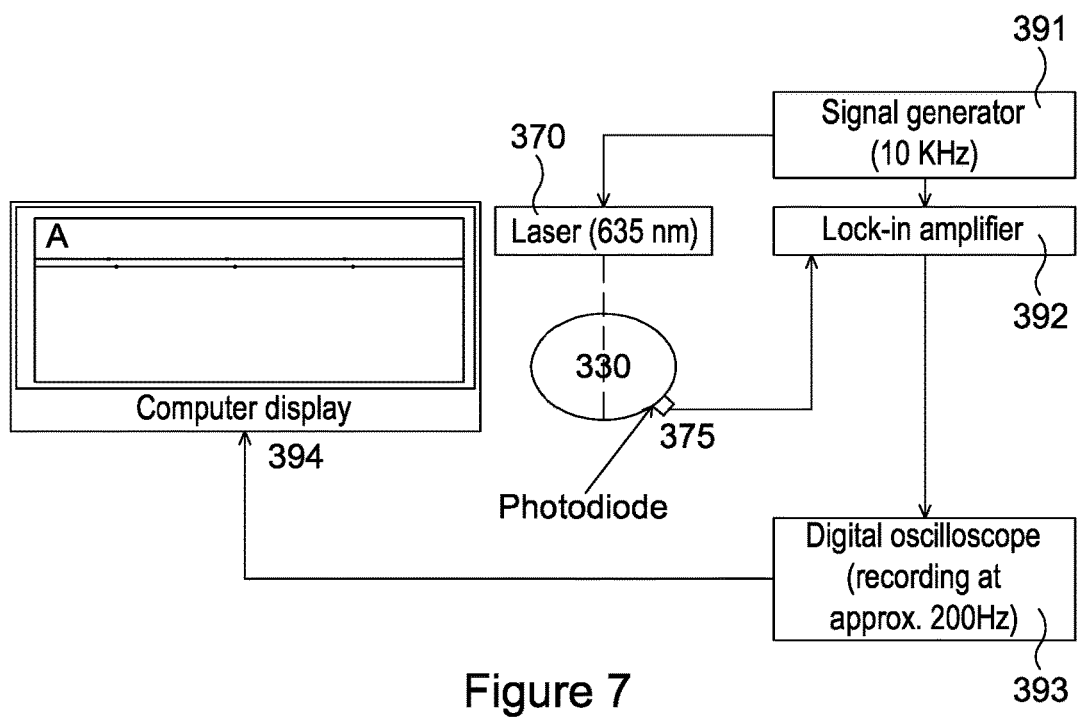
FIG. 7 is a block diagram of a detection and analysis system for use with the apparatus of FIG. 4 or FIG. 6.

FIG. 7 shows a detection and analysis system 300 for use with the apparatus of FIG. 4 or FIG. 6.

In FIG. 7 the detection chamber 330 may be any one of the detection chambers 130, 140, 230 or 240 of FIGS. 1 and 5. Similarly, the light source 370 may be any one of the laser units 172, 182, 272, 282 of FIGS. 4 and 6. The photodetector 375 may be any one of the detectors 175, 185, 275, 285 of FIGS. 4 and 6, and in this embodiment has a photodiode.

The laser unit 370 is connected to a signal generator 391 that is adapted to control a modulation frequency and phase of the laser output. The photodiode 375 is connected to a lock-in amplifier 392. An input of the amplifier 392 is connected to the signal generator 391. An output of the amplifier 392 is connected to a digital oscilloscope 393. The lock-in amplifier 392 uses phase-sensitive detection to single out a component of the signal at a specific reference frequency and phase, in this case the modulation frequency that is set by the signal generator 391. Noise signals, at frequencies other than the reference frequency, are rejected and do not affect the measurement. An output from the digital oscilloscope 393 is fed to a computer display 394.

The signal generator 391 is arranged to modulate the output frequency of the laser source 370. As an example, the laser may be modulated at a frequency of 10 kHz with a phase of +169°, and a peak-to-peak amplitude of 200 mV. The detected signal is filtered by the lock-in amplifier 392. The lock-in amplifier 392 filters the detected signal from the photodiode 375. The lock-in amplifier 392 synchronizes the detected signal with the modulation applied to the light source 370 to provide a dampening system that eliminates unwanted noise, for example, background electrical or luminous noise. The filtered signal is sent to the digital oscilloscope 393 to be recorded. The recorded signal can be displayed on the computer display 394.

Raw data is collected by the digital oscilloscope 393. Typically around 16,000 data points are collected for every 30 second experiment. The data is exported to a calculation suite in a processor which returns the averages (mean, median, mode) and the standard deviation of the data points. If the standard deviation is above a threshold (indicating aberrations from the norm in the data) the data is discarded. The mean of each experiment is selected. The experiments have between 3 and 89 technical replicates, which are collected and tabulated. The standard error from the mean of these averages is calculated and charted as error bars along with the data. Once the data is graphed, a function, such as a standard Gompertz, is fitted to the data in order to estimate future outcomes of experiments such as inocula sizes. Any other suitable data collection and analysis procedure may be used in alternative embodiments.

Figure 8:
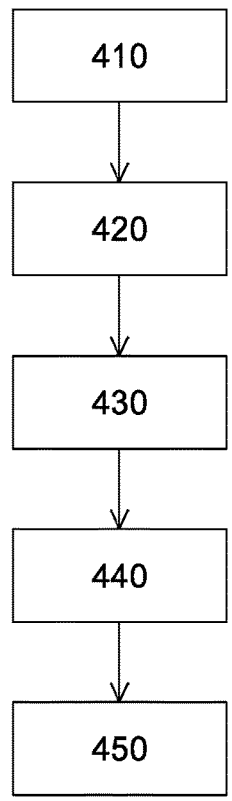
FIG. 8 is a block diagram of a method for measuring a sample according to an embodiment of the present invention.

FIG. 8 shows a block diagram of a method 400 for measuring a sample according to an embodiment of the present invention. The method may for example be implemented by using the apparatus of FIG. 4 or FIG. 6.

In a first step 410, a biological sample is introduced into a specimen chamber 110,210 of cartridge 100,200.

In a second step 420, microorganisms are allowed to pass from the specimen chamber 110,210 through a semipermeable membrane 120,220 into a first detection chamber 130, 233.

The sample in the first detection chamber is then tested over a period of time, 430, to determine the presence or absence of microorganisms such as bacteria, and the amount of microorganisms, by emitting light in the first detection chamber 130,230 so that the light passes through and is scattered by the sample, detecting light scattered in the first detection chamber 130,230 and analysing the detected light, as explained above in detail.

It will be appreciated that the primary purpose of this step is to detect the presence and the amount of pathogenic or infectious microorganisms, rather than any organisms that may be present in the sample as a result of their natural occurrence in a subject's clinical sample. Thus, prior calibration may be carried out in order to determine a measured signal that would correspond to an upper limit of a subject's typical level of naturally occurring bacteria, so as to provide a value of a signal that corresponds to a "base" level of naturally occurring bacteria. Alternatively, the "base" level of naturally occurring bacteria may be obtained from existing literature, and a corresponding "base" signal may be generated by extrapolation or experimentation. Any measured signal below the "base" signal may be interpreted as a "negative" result, i.e., as an indication that the sample does not contain an infectious amount of microorganisms.

If an infectious or pathogenic amount of microorganisms is measured in step 430, at least part of the sample is transferred in step 440 from the first detection chamber 130,230 to a plurality of second detection chambers 140, 240, as explained above in detail. Upon transfer, the sample is exposed to a different antibiotic in each second detection chamber 140,240. One of the second detection chambers 140a,240a does not contain any antibiotic and acts as a control chamber.

Each chamber 140,240 is then monitored by analysing the scattered light detected from each second detection chamber 140,240 over a period of time, in step 450. A change in the signal in the control chamber 140a,240a, and in particular an increase measured scattered light in the control chamber 140a240a, is indicative of growth of microorganisms over that period of time. This is compared with the measured scattered light in the other second chambers 140b-140m, 240a-240m, and the absence of an increased signal over the period of time in one or more chambers is indicative of the absence of growth of the microorganisms over that period of time, and thus of the susceptibility of the microorganism to the substance, e.g. antibiotic, present in one or more chambers.

As a result, the present apparatuses and methods provide a simple, effective, reliable and fast way of assessing both the possible presence of pathogenic microorganisms in a subject's clinical sample, and also the susceptibility of the microorganisms to a number of possible therapeutic substances.

It will be appreciated that the described embodiments are not meant to limit the scope of the present invention, and the present invention may be implemented using variations of the described examples.

What is claimed is:

1. An apparatus comprising a one-piece cartridge, the cartridge comprising:
    a specimen chamber for receiving a sample;
    a first detection chamber for receiving microorganisms and configured to allow detection of the microorganisms via detection of scattered light from the first detection chamber;
    a medium comprising a semipermeable membrane configured to permit passage of the microorganisms from the sample through the medium into the first detection chamber;
    wherein the specimen chamber and the first detection chamber form separate chambers, the one-piece cartridge having walls defining the specimen chamber and the first detection chamber, respectively; and
    at least one second detection chamber configured to allow detection of the microorganisms via detection of scattered light from the at least one second detection chamber, wherein the at least one second detection chamber contains a substance potentially capable of inhibiting growth of the microorganisms, the substance comprising an antibiotic in freeze-dried form.

2. An apparatus according to claim 1, wherein the scattered light from the first detection chamber and the second detection chamber comprises light that has been transmitted into a respective detection chamber and scattered by the microorganisms in the detection chamber.

3. An apparatus according to claim 1, wherein the semipermeable membrane has a pore size of about 2 μm-10 μm.

4. An apparatus according to claim 1, wherein the first detection chamber is configured to allow quantitative measurement of the microorganisms via detection of the scattered light from the first detection chamber.

5. An apparatus according to claim 1, wherein the at least one second detection chamber is configured to allow quantitative measurement of the microorganisms via detection of the scattered light from the at least one second detection chamber.

6. An apparatus according to claim 1, wherein the sample is a primary or clinical sample.

7. An apparatus according to claim 1, wherein an opening is provided between the specimen chamber and the first detection chamber, and wherein the semipermeable medium is provided within the opening and/or covers substantially the whole area of the opening.

8. An apparatus according to claim 1, wherein the first detection chamber contains a bacterial growth fluid.

9. An apparatus according to claim 1, wherein the apparatus further comprises a first light source for emitting light into the first detection chamber.

10. An apparatus according to claim 9, wherein the first light source comprises a laser or a LED.

11. An apparatus according to claim 9, wherein the first detection chamber is capable of reflecting light emitted by the first light source inside the first detection chamber.

12. An apparatus according to claim 9, wherein the first detection chamber has a first light entry aperture to allow light emitted by the first light source to enter the first detection chamber.

13. An apparatus according to claim 12, wherein the first detection chamber has a first light exit aperture located opposite the first light entry aperture.

14. An apparatus according to claim 9, further comprising at least one second light source for emitting light into one or more of the at least one second detection chambers.

15. An apparatus according to claim 14, wherein each second detection chamber has a respective light entry aperture to allow the at least one second light source to emit light into the at least one second detection chamber.

16. An apparatus according to claim 15, wherein the at least one second detection chamber has a respective light exit aperture located opposite the respective light entry aperture.

17. An apparatus according to claim 9, wherein the first light source is used to emit the light into the at least one second detection chamber.

18. An apparatus according to claim 1, further comprising a first detector for detecting the scattered light from the first detection chamber and generating a signal indicative of the scattered light from the first detection chamber.

19. An apparatus according to claim 18, wherein the first detection chamber has a light detection outlet associated with the first detector.

20. An apparatus according to claim 1, wherein the at least one second detection chamber includes a plurality of second detection chambers.

21. An apparatus according to claim 1, wherein the at least one second detection chamber is configured to be in fluid communication with the first detection chamber.

22. An apparatus according to claim 1, further comprising a transfer mechanism to allow transfer of at least part of the sample from the first detection chamber to the at least one second detection chamber.

23. An apparatus according to claim 22, wherein the transfer mechanism comprises one or more valves.

24. An apparatus according to claim 1, further comprising at least one second detector for detecting scattered light in of the at least one second detection chamber and generating a signal indicative of the scattered light detected by the at least one second detector.

25. An apparatus according to claim 24, wherein the at least one second detection chamber has a detection outlet associated with the at least one second detector.

26. An apparatus according to claim 1, wherein the at least one second detection chamber is capable of reflecting light emitted by the light source into the second detection chamber.

27. A one-piece cartridge comprising:
a specimen chamber for receiving a sample;
a first detection chamber for receiving microorganisms and configured to allow detection of the microorganisms via detection of scattered light from the first detection chamber;
a medium comprising a semipermeable membrane configured to permit passage of the microorganisms from the sample through the medium into the first detection chamber;
wherein the specimen chamber and the first detection chamber form separate chambers, the one-piece cartridge having walls defining the specimen chamber and the first detection chamber, respectively; and
at least one second detection chamber configured to allow detection of the microorganisms via detection of scattered light from the second detection chamber, wherein the at least one second detection chamber contains a substance potentially capable of inhibiting growth of the microorganisms, the substance comprising an antibiotic in freeze-dried form.

28. A method for monitoring a biological material, the method comprising:
introducing a biological sample into a specimen chamber;
allowing selective passage of microorganisms from the biological sample in the specimen chamber through a medium comprising a semipermeable membrane into a first detection chamber;
emitting light into the first detection chamber so that the light at least partly passes through and is scattered by the biological sample, and detecting light scattered in the first detection chamber; and
emitting light into at least one second detection chamber so that the light at least partly passes through and is scattered by the biological sample, and detecting light scattered in the at least one second detection chamber, wherein the at least one second detection chamber contains a substance potentially capable of inhibiting growth of the microorganisms, the substance comprising an antibiotic in freeze-dried form.

29. A method according to claim 28, further comprising analysing the detected scattered light from the first detection chamber, wherein the detected scattered light from the first detection chamber is indicative of an amount of microorganisms in the biological material.

30. A method according to claim 28, further comprising transferring at least part of the biological sample from the first detection chamber to the at least one second detection chamber when an amount of the microorganisms in the first detection chamber is an infectious or pathogenic amount.

31. A method according to claim 28, further comprising monitoring the detected scattered light from the at least one second detection chamber over time, or detecting the scattered light from the at least one second detection chamber in response to expiry of a predetermined period of time after introduction of the biological sample.

32. A method according to claim 28, further comprising analysing the detected scattered light from the first detection chamber so as to allow quantitative measurement of the microorganisms.

33. A method according to claim 28, further comprising analysing the detected scattered light detected from the at least one second detection chamber so as to allow quantitative measurement of the microorganisms.

* * * * *